United States Patent [19]
Kenda

[11] Patent Number: 5,255,689
[45] Date of Patent: Oct. 26, 1993

[54] INTERCEPTING APPARATUS SAMPLING URINE FOR EXAMINATION PURPOSES

[76] Inventor: Rajko Kenda, Staniceva 5b, Ljubljana, Spratly Islands, 61000

[21] Appl. No.: 869,131

[22] Filed: Apr. 15, 1992

[30] Foreign Application Priority Data

Apr. 20, 1991 [YU] Yugoslavia .............................. 714/91

[51] Int. Cl.$^5$ ............................. A61B 5/00; A61F 5/44
[52] U.S. Cl. ..................................... 128/762; 128/767; 604/352; 4/144.2
[58] Field of Search ................ 128/760, 761, 762, 767; 141/331, 1; 604/352, 327, 349; 4/144.2, 144.3, 144.4

[56] References Cited

U.S. PATENT DOCUMENTS

| | | |
|---|---|---|
| 3,161,891 | 12/1964 | Bauman . |
| 3,292,626 | 12/1966 | Schneider . |
| 3,295,145 | 1/1967 | Ericson . |
| 3,635,091 | 1/1972 | Linzer et al. ......................... 128/767 |
| 3,982,898 | 9/1976 | McDonald . |
| 4,094,020 | 6/1978 | Franklin . |
| 4,301,812 | 11/1981 | Layton et al. . |
| 4,305,161 | 12/1981 | Diaza . |
| 4,457,314 | 7/1984 | Knowles . |
| 4,492,258 | 1/1985 | Lichtenstein et al. ............... 141/331 |
| 4,494,581 | 1/1985 | Gordon ................................. 141/331 |
| 4,495,951 | 1/1985 | Kenda . |
| 4,804,377 | 2/1989 | Hanifl et al. .......................... 128/767 |

Primary Examiner—Stephen C. Pellegrino
Assistant Examiner—Gary Jackson
Attorney, Agent, or Firm—Keck, Mahin & Cate

[57] ABSTRACT

According to the invention the inflow funnel/duct insertion 10 stable in its shape is by its funnel part 15 matingly inserted into an entering chamber 13 of a receptacle 1 which is unstable in its shape and is suitably made of foil, with a socket 17 of the funnel/duct insertion 10 provided for receiving a test tube 21 projects from the receptacle 1. Between a connection streak 11 arranged at the transition of the funnel part 15 to the socket 17 of the funnel/duct insertion 10, the connection streak 11 forming a circumferential interconnection of the funnel/duct insertion 10 and the receptacle 1, and a further connection streak 12 arranged at a distance from the firstmentioned connection streak 11 by height below the latter, the connection streak 12 forming a further interconnection between the funnel/duct insertion 10 and the receptacle 1, a through bore 19 is foreseen which interconnects a depositing chamber 14 of the receptacle 1 separated from the entering chamber 13 of the receptacle 1 by a continuous welded joint 5 which binds a first upright side of the receptacle 1 with the connection streak 11. The funnel/duct insertion 10 comprises an inclined-axis funnel part 15, to whose discharging orifice an upright-axis immerse duct 16 is connected, whose length section abutting on the funnel part 15 is encompassed by a socket 17 arranged eccentrically with respect to the immerse duct 16. The generatrixes of the funnel part 15, those of the immerse duct 16 and the socket 17, which each coincide with the second upright side of the receptacle 1, located off the attaching recess 3 of the receptacle 1 mutually coincide or are straight, respectively.

4 Claims, 2 Drawing Sheets

INTERCEPTING APPARATUS SAMPLING URINE FOR EXAMINATION PURPOSES

FIELD OF THE INVENTION

The invention belongs to the field of medicine, particularly to the field of instruments, especially instruments for the diagnosis, in the case related to, particularly apparatus for receiving/intercepting urine.

Besides, the invention belongs to the field of physics, in the given case to the field of instruments and, in connection therewith, to the field of examinations, particularly examinations relating to searching or analyzing materials by determining chemical or physical properties thereof and, in the instant case, it belongs to the field of taking and preparing, respectively, samples, i.e. samples in the form of liquids and particularly streaming liquids, respectively.

BACKGROUND OF THE INVENTION

The invention relates to an intercepting apparatus which enables sampling urine for examination purposes, particularly of patients whose urinating can, in principle, not be realized on the basis of recommendation of medical staff, specially of small children as well as of adults who are, due to whatever disability relating either to the mind or to the body, on the initiative of a member of medical staff not able to independently prepare an acceptable sample of own urine, whereby for laboratory or bacteriological examinations there is required separation of the last portion of urine, which is decisive for examination purposes, from the remaining portion of urine of a single miction, not appropriate for examination, and whereby an assembly of a detachable container, suitably a test tube, and an inflow funnel/duct constituently connected to the test tube is used for physically dividing the total quantity of urine of a single miction to two portions and for sampling same.

Particularly in pediatrics there is for sampling urine needed to carry out laboratory and bacteriological examinations, generally known the use of receptacles made of plastic foil, so-called bags, which are by means of a self-adhesive annular section foreseen at the attaching orifice of the receptacle adhered around the patient's urinary orifice, and are thus arranged prepared to intercept urine if it starts to flow and when it is discharged.

Considering the circumstance that such a receptacle contains the whole quantity of urine, such method of gaining urine samples is not appropriate for carrying out specific laboratory and bacteriological examinations.

It is known from U.S. Pat. No. 4,495,951 to Kenda that to an adapter made of plastic foil and providing a self-sealing annular area for attaching the intercepting apparatus to a patient there is in downstream manner attached an apparatus assembly for separating the quantity of urine to three or two portions, the former option having been declared as preferable therein.

It is a disadvantage of the referred-to solution, whose operation is based on the gravitation force, that the positioning of the apparatus is conditioned by a fully defined, essentially sitting, patient position which can only be realized by means of a special chair.

From U.S. Pat. No. 4,094,020 to Franklin there is known a urine specimen collector which is from the outside composed of two upright tubes of different heights and arranged alongside one another so as to be leveled at the bottom, and interconnected by a duct in the area of the upper end of the lower tube, said tubes being used in the upright position in a combination with a toilet. The lower tube provides a tube segment open upwards and foreseen to be engaged around a male or a female, respectively, external urinary organ, the tube segment receiving a test tube from below, and also provides a draining tube arranged within the nominal diameter of said tube segment as well as along the prevailing extent of the inner height of the test tube, said draining tube being attached to an interconnecting opening foreseen between said tubes. The other tube of the two is open at the bottom.

The reference solution is obviously aimed to be used by an adult sensible patient whose locomotion has not been impaired. Said solution as such does not meet the aim defined by the introduction given above.

In view of the prior art analyzed, there existed a problem, namely how to design an apparatus such as defined by the above introduction, which retained a simple arrangement typical for foil receptacles, but nevertheless made possible separation of urine of a single miction to two portions with one of them intercepted in a manner suitable for transportation into the laboratory and obviating the necessity of the patient sitting position at interception of urine. In other words, there existed a problem of how to combine the features of a simple, generally known bag which, in principle, required no special engagement by the nursing personnel, and to separate a sample of urine according to the teachings of US'020.

SUMMARY OF THE INVENTION

According to the invention the problem has been solved in that a funnel/duct insertion stable in its shape has by its funnel part been matingly inserted into an entering chamber of a receptacle which is unstable in its shape and is suitably made of foil, with a socket of said funnel/duct insertion provided for receiving a test tube projecting from the receptacle.

Hereby, between a connection strip arranged at the transition of the funnel part of the funnel/duct insertion to the socket of the funnel/duct insertion, the connection streak forming a circumferential interconnection of the funnel/duct insertion and the receptacle, and a further connection streak arranged at a distance from the firstmentioned connection streak by height below the latter, with the connection streak referred-to forming a further interconnection between the funnel/duct insertion and the receptacle, a through bore is foreseen which interconnects a depositing chamber of the receptacle, separated from the entering chamber of the receptacle by a continuous welded joint which binds a first upright side of the receptacle with the first mentioned connection streak.

In a suitable embodiment of the invention said funnel/duct insertion comprises an inclined-axis funnel part, to whose discharging orifice an upright-axis immerse duct is connected, whose length section abutting on the funnel part is encompassed by a socket arranged eccentrically with respect to the immerse duct.

Considering several aspects it is advantageous that the generatrixes of the funnel part, those of the immerse duct and the socket, which each coincide with a second upright side of the receptacle, positioned off the attaching recess of the receptacle, mutually coincide or are straight, respectively.

BRIEF DESCRIPTION OF THE DRAWINGS

Hereafter the invention is disclosed in more detail on the basis of an embodiment represented in a drawing attached. There is shown in:

FIG. 3 is a perspective view of the apparatus of FIG. 1, partly in cross-section.

FIG. 4 is a perspective view of the apparatus of FIG. 1, taken from the side opposite to that shown in FIG. 3.

DETAILED DESCRIPTION OF THE PREFERRED EMBODIMENTS

Figure 1:
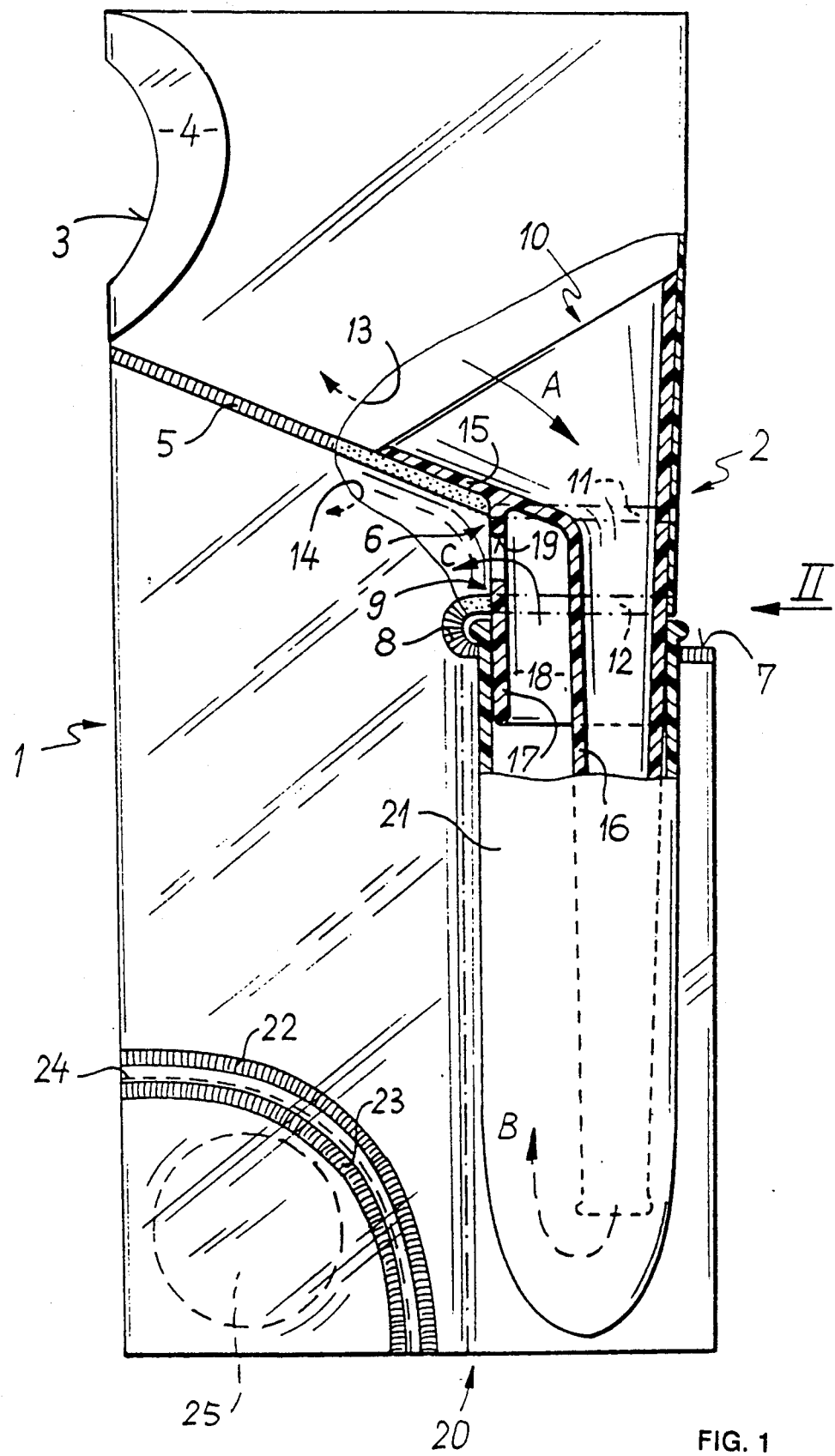
FIG. 1 an elevational view, partly in vertical section, of an apparatus referred to, the apparatus in a state prior to an attachment to a patient.
Figure 2:
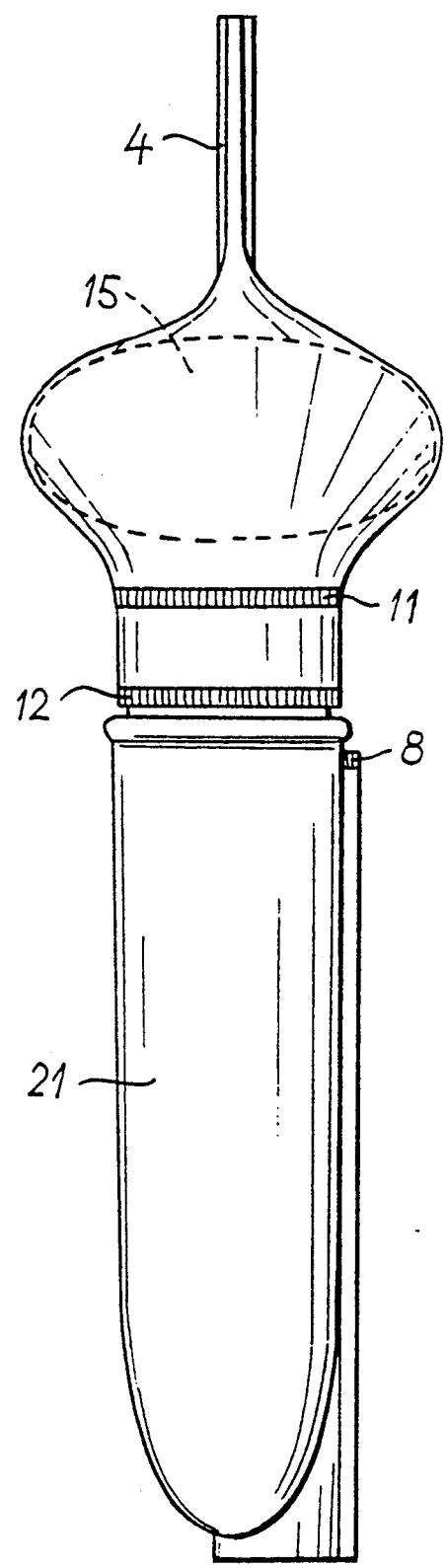
FIG. 2 the apparatus of FIG. 1 as seen in the direction of arrow II of FIG. 1.

FIGS. 1 to 4 illustrate an intercepting apparatus for sampling urine.

An intercepting apparatus for sampling urine for examination purposes according to the invention consists of a receptacle 1, which is flexible as such and is in analogy to wrapping bags suitably made of plastic foil, and further consists of a functional assembly 2 whose form as such is stable.

In its original state and prior to be used, the receptacle 1 is in its assembled state essentially designed as an upright or flattened, respectively, hose or double foil, respectively. Due to the circumstance that by the technique of intercepting and catching, respectively, urine samples there exist no special conditions as to the outline of the flattened receptacle 1 (with a mere exception of a detail at the inlet or receiving, respectively, recess of the receptacle 1), the outline of the receptacle 1 is essentially subordinated to technological and manufacturing aspects. The embodiment represented is thus based on a supposition that the receptacle 1 is formed by cutting by welding a band-shaped or a strip-shaped foil starting material which suitably results in that prior to assembling thereof with the functional assembly 2 the receptacle 1 as such is designed square and that it in one of elevational views also retains the features of a square design after the apparatus has been completed.

Along a first upright side of the square outline of the flattened receptacle 1 there is in the area close to its upper transversal side arranged a suitably arcuate attaching recess 3 designed and measured so that in a spread state of the receptacle 1 there is created a suitable circular or oval opening for admitting the urinary organ of a patient. For practical attaching reasons, the border encompassing the recess 3 is in known manner provided with an adhesive layer (not specially shown in the drawing), which in the state prior to the use of the apparatus referred-to is covered by a protective foil 4 adapted by shape, which by being bent at the corresponding upright side of the receptacle 1 stretches from one side of the receptacle 1 to the other side thereof.

In the area below the attaching recess 3 and below the protective foil 4 belonging to the former there is, starting at the first upright side of the receptacle 1, drawn a continuous welded joint 5 which traverses a part of the width of the receptacle 1 and is hereby suitably inclined downwards, it essentially also tightly interconnecting the front and the rear plane sections of the receptacle 1. As a consequence, there appears an unwelded area of the receptacle 1 between the free, lower end of the continuous welded joint 5 and the opposite, i.e. second, upright side of the receptacle 1, said unwelded area forming a transition 6 in the assembled state of the apparatus.

In the area below the transition 6 the receptacle 1 provides a further recess 7, the length of the recess 7 proceeding from the second upright side of the receptacle 1, in the given case proceeding perpendicularly to said side, and being essentially straight and terminating arcuately, being preferably larger than the extent of the transition 6 measured in parallel to the recess 7. Starting at the upright side of the receptacle 1, at the side of the recess 7 remote from the transition 6, the border of the recess 7 is provided with a welded joint 8 which also extends along the arcuate termination of the recess 7 and beyond up to the side of the recess 7 closer to the transition 6, where the welded joint 8 terminates in the area of the vertical projection of the end of the continuous welded joint 5, which defines the transition 6. Between the end of the welded joint 8 and the second upright side of the receptacle 1 there evidently exists a transition 9 analogous to the transition 6.

From the first side of the receptacle 1, on which the access recess 3 is forseen, there is through the two transitions 6 and 9 of the receptacle 1 inserted a stable funnel/duct insertion 10 which is in the area of the transition 6 interconnected with the receptacle 1 by an annular welded/sticking connection strip 11. Thereby, the inside of the receptacle 1 is divided to an upper, entering chamber 13, and a lower, depositing chamber 14.

The funnel/duct insertion 10 comprises a funnel part 15 and, attached thereto, an immerse duct 16 and a socket 17.

In the proposed embodiment the funnel part 15 is designed on the basis of an inclined axis by having circular circumference, with the axis approximately directed to the access recess 3, the conicity of the funnel part 15 being in the scope of the manufacturing and assembling circumstances suitably adapted to the angle formed by the inclined continuous welded joint 5 and the second upright side of the receptacle 1. In the preferable design of the apparatus the funnel part 15 of the funnel/duct insertion 10 is interconnected with the wall of the receptacle 1 by means of gluing.

The immerse duct 16 of the funnel/duct insertion 10 is connected directly to the throat section of the funnel part 15. Hereby, the axis of the immerse duct 16 is essentially vertical, i.e., the axes of the funnel part 15 and the one of the immerse duct 16 cross each other. In a preferable design the parts 15, and 16 of the funnel/duct insertion 10 are arranged so that the generatrixes thereof coinciding with the second upright side of the receptacle 1 are mutually straight. The axial extension of the immerse duct 16 essentially exceeds the axial extension of the funnel part 15 and is determined so that it reaches nearly up to the lower horizontal side of the receptacle 1. Merely for the reasons of manufacture, the immerse duct 16 is slightly conical in side elevation.

The socket 17 of the funnel/duct insertion 10 is, in principle, arranged in the same manner as the immerse duct 16, it being positioned eccentrically with respect to the latter and being of a greater diameter in comparison to the latter. In a preferable embodiment the generatrix of the socket 17 coinciding with the second upright side of the receptacle 1 coincides with the generatrix of the same location of the immerse duct 16, otherwise the socket 17 is bound to the outer surface of the funnel part 15. The outer diameter of the socket 17 which, as such, is slightly conical from the outside in the direction to its lower end, at the positions of the connection strips 11 and 12 corresponds to the nominal diameters of the transitions 6 and 9. In such starting condition the socket 17 and the immerse duct 16 form a channel 18 having a sickle-shaped cross-section. In the plane of the greatest radial clearance of the channel 18 there is by the height between the connection strips 11, 12 in the wall of the socket 17 arranged a through bore 19 representing a communication between the channel 18 and the depositing chamber 14 of the receptacle 1. The length of the socket 17 is defined so that a part of the socket 17 projects from below the connection streak 12, it crossing the recess 7 of the receptacle 1 and partly covering the altitude area of the receptacle 1 below the recess 7, but it is essentially smaller than the length of the immerse duct 16.

The embodiment disclosed is designed on a practical supposition that the receptacle 1 is manufactured of a foil semi-product, whose upper and lower sides are equal. After a horizontal recess 7 has been made from the second upright side of the receptacle 1 and after the funnel/duct insertion 10 has been inserted into the receptacle 1 according to the above disclosure, the funnel/duct insertion 10 in principle (disposition inconsistency) strikes the upright section of the receptacle 1 residing below the recess 7. According to the invention, said disposition inconsistency is simply avoided in that the upright referred-to section of the receptacle 1 is on the location of the vertical projection 20 of the arcuate part of the welded joint 8 by using the flexibility of the foil material of the receptacle 1 deflected from the general plane of the receptacle 1, which is the axial plane of the funnel/duct insertion 10, following deflection said upright section being arranged tangentially with respect to the funnel/duct insertion 10. Within an altered design of the receptacle 1, also possible according to the teachings of the invention, said deflection and deformation of a part of the receptacle 1 can be avoided if a part of the second upright side of the receptacle 1 coincides with the location of said vertical projection 20.

Onto the socket 17 of the funnel/duct insertion 10 a test tube 21 is attached whose inner diameter is adapted to the outer diameter of the part of the socket 17, projecting below the connection streak 12, and whose length is adapted to receive the immerse duct 16 of the funnel/duct insertion 10 in a manner that the bottom of the test tube 21 is appropriately removed from the orifice of the immerse duct 16.

The features disclosed above, actually characterize the apparatus according to the invention in its entireness. Considering the circumstance that in practice not the entire apparatus, but merely the test tube containing urine will be transported to a laboratory, there is according to the invention as a part belonging to the apparatus also foreseen an appropriate sterile cap for closing the test tube and insulating its content. As a mere illustration of one of embodiments, the lower corner section of the receptacle 1, in the embodiment shown the one located at the first upright side, is regarding communication by means of two auxiliary welded joints 22, 23 drawn in the form of arcs between the upright and the horizontal sides of the receptacle 1, as well as by means of a perforation 24 arranged therebetween separated from the remaining part of the receptacle 1, in said corner section there being accomodated a cap 25 for the test tube 21.

When using the apparatus the protective foil 4 of the access recess 3 is removed, the receptacle 1 is spread around the recess 3 and attached around the urinary organ of the patient in principle, but not obligatorily, in hanging state of the apparatus. It is convenient if at this moment the cap 25 for the test tube has already been separated from the receptacle 1.

At miction (urinating) urine flows through the entering chamber 13 of the receptacle 1 into the funnel part 15 (arrow A), then flowing through the immerse duct 16 and striking the bottom of the test tube 21 (arrow B), thereafter ascending along the outer side of the immerse duct 16 inside the test tube 21 to reach the channel 18 and leaving same through the through bore 19 (arrow C) to finally reach the depositing chamber 14 of the receptacle 1. Subsequent urine quantities displace the preceeding ones, and according to this supposition there remains in the test tube 21 the lastcoming quantity of urine, which also happens in the case that at taking a sample the test tube 21 was, e.g., not in upright position, which is to be expected in circumstances as defined in the introduction.

What I claim is:

1. An intercepting apparatus for sampling urine for examination purposes and for separation of a last portion of urine from a first portion of urine of a single miction, comprising in combination:

a receptacle (1);

a test tube (21), and an inflow funnel/duct insertion (10) connected to the test tube for physically dividing the total quantity of urine of a single motion into two portions, wherein the inflow funnel/duct insertion (10) comprises a funnel part (15) matingly inserted into an entering chamber (13) of the receptacle (1) and a socket (17) adapted for receiving the test tube (21) extending from the receptacle (1), said funnel part (15) comprising a duct (16) integral with said inflow funnel/duct insertion (10) extending longitudinally into said test tube (21), a neck portion and a bore (19) in said neck portion, wherein said funnel part receives inflow of urine, a first portion of urine passing through said bore into said receptacle, and a last portion of urine remaining in said test tube.

2. An intercepting apparatus of claim 1, wherein a first connection strip (11) is arranged at a transition between the funnel part (15) and to the socket (17) of the funnel/duct insertion (10), the first connection strip (11) forming a circumferential interconnection of the funnel/duct insertion (10) and the receptacle (1), and a second connection strip (12) is spaced below the first connection strip (11), the second connection strip (12) forming a further interconnection between the funnel/duct insertion (10) and the receptacle (1), a through bore (19) interconnecting a depositing chamber (14) of the receptacle (1) separated from the entering chamber (13) of the receptacle (1) by a continuous welded joint (5) which binds a first upright side of the receptacle (1) with the first connection strip (11).

3. An intercepting apparatus according to claim 1, wherein the funnel/duct insertion (10) comprises an inclined-axis funnel part (15), having a discharging orifice to which an upright-axis immerse duct (16) is connected, wherein a length section of said immerse duct (16) abutting on the funnel part (15) is encompassed by a socket (17) arranged eccentrically with respect to the immerse duct (16).

4. An intercepting apparatus according to claim 1, wherein generatrixes of the funnel part (15), of the immerse duct (16) and the socket (17), which each coincide with a second upright side of the receptacle (1), located off an attaching recess (3) of the receptacle (1) and mutually coincide or are straight.

* * * * *

UNITED STATES PATENT AND TRADEMARK OFFICE
CERTIFICATE OF CORRECTION

PATENT NO. : 5,255,689
DATED     : October 26, 1993
INVENTOR(S) : Rajko KENDA

It is certified that error appears in the above-identified patent and that said Letters Patent is hereby corrected as shown below:

On the title page,
In [76], change "Spratly Islands" to --Slovenia--

Signed and Sealed this

Twenty-fourth Day of May, 1994

Attest:

BRUCE LEHMAN

Attesting Officer

Commissioner of Patents and Trademarks